(12) United States Patent
Russell

(10) Patent No.: US 7,554,666 B2
(45) Date of Patent: Jun. 30, 2009

(54) SENSOR WITH OPTICAL PRESSURE TRANSDUCER AND METHOD OF MANUFACTURING A SENSOR COMPONENT

(75) Inventor: James T. Russell, Bellevue, WA (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 11/805,074

(22) Filed: May 22, 2007

(65) Prior Publication Data

US 2007/0273887 A1 Nov. 29, 2007

Related U.S. Application Data

(60) Provisional application No. 60/808,312, filed on May 25, 2006.

(51) Int. Cl.
*G01B 9/02* (2006.01)

(52) U.S. Cl. .......................... 356/450; 600/532; 73/700

(58) Field of Classification Search ................. 356/480, 356/481, 517, 519, 450; 385/13; 600/532; 73/700

See application file for complete search history.

(56) References Cited

U.S. PATENT DOCUMENTS

| | | | |
|---|---|---|---|
| 4,706,502 A | 11/1987 | Jones et al. | |
| 4,859,858 A | 8/1989 | Knodle et al. | |
| 4,859,859 A | 8/1989 | Knodle et al. | |
| 5,127,173 A * | 7/1992 | Thurston et al. | ............... 73/202 |
| 5,153,436 A | 10/1992 | Apperson et al. | |
| 5,693,944 A | 12/1997 | Rich | |
| 5,789,660 A * | 8/1998 | Kofoed et al. | ................. 73/23.2 |
| 6,312,389 B1 * | 11/2001 | Kofoed et al. | ................ 600/532 |
| 6,325,978 B1 | 12/2001 | Labuda et al. | |
| 6,683,679 B2 | 1/2004 | Belenkii | |
| 6,691,579 B2 * | 2/2004 | Orr et al. | ....................... 73/700 |
| 6,968,741 B2 * | 11/2005 | Orr et al. | ....................... 73/700 |
| 7,174,789 B2 * | 2/2007 | Orr et al. | ....................... 73/700 |
| 2002/0159671 A1 | 10/2002 | Boyd et al. | |
| 2003/0101827 A1 * | 6/2003 | Cha et al. | ................. 73/861.66 |
| 2005/0017313 A1 | 1/2005 | Wan | |
| 2006/0082256 A1 | 4/2006 | Bibl et al. | |
| 2007/0261486 A1 * | 11/2007 | Fallet | ....................... 73/152.29 |

FOREIGN PATENT DOCUMENTS

WO WO 2005108932 A1 * 11/2005

OTHER PUBLICATIONS

Kim et al., "Fabry-Perot Based Pressure Transducers", weewave.mer.utexas.edu/MED_files/MED_research/F_P_sensor_folder/FP_pressu..., 2005.
Miller, "Flow Measurement Engineering Handbook", 1989, USA.

* cited by examiner

*Primary Examiner*—Tarifur Chowdhury
*Assistant Examiner*—Jonathan M Hansen

(57) ABSTRACT

An airway adapter that comprises a housing and a pressure transducer. The housing comprises a flow path having a first end and a second end, a first pressure port that communicates with the flow path, and a second pressure port that communicates with the flow path. The first pressure port is spaced apart from the second pressure port. The flow restriction is disposed in the flow path between the first and second pressure ports that creates a pressure differential therebetween. The pressure transducer generates a signal that reflects the differential pressure created by the flow restriction between the first and second pressure ports, wherein the pressure transducer comprises an optical interferometer.

9 Claims, 16 Drawing Sheets

SENSOR WITH OPTICAL PRESSURE TRANSDUCER AND METHOD OF MANUFACTURING A SENSOR COMPONENT

CROSS-REFERENCE TO RELATED APPLICATIONS

This application claims priority under 35 U.S.C. § 119(e) from provisional U.S. patent application No. 60/808,312, filed May 25, 2006, the contents of which are incorporated herein by reference.

BACKGROUND OF THE INVENTION

1. Field of the Invention

The invention relates to a method of manufacture of a interferometric sensor component and the implementation of an interferometer to detect a pressure differential in a gas flow path.

2. Description of the Related Art

Respiratory gas flow measurement during the administration of anesthesia, in intensive care environments, and in monitoring the physical condition of athletes and other individuals prior to and during the course of training programs and other medical tests provides valuable information for assessment of cardiopulmonary function and breathing circuit integrity. Many different technologies have been applied to create a flow meter that attempts to meet the demanding requirements of these environments.

Although various other types of pressure measurement apparatus are known, differential pressure flow meters have conventionally been used to obtain respiratory flow measurements. While pressure monitoring is typically performed to measure delivered (i.e., inspired) and exhaled volume by monitoring respiratory mechanics parameters, such as airway pressures, flow rates, and breath volumes, clinicians can better provide quality health care to patients requiring breathing assistance. Additionally, pressure monitoring may be used in conjunction with respiratory gas measurements to assess other respiratory parameters, such as oxygen consumption, carbon dioxide elimination, and even cardiac output or pulmonary capillary blood flow.

Some differential pressure flow meters operate on the basis of Bernoulli's principle: the pressure drop across a restriction is proportional to the volumetric flow rate of the air. The relationship between flow and the pressure drop across a restriction or other resistance to flow is dependent upon the design of the resistance. In some differential pressure flow meters, which are commonly termed "pneumotachs," the flow restriction has been designed to create a linear relationship between flow and a pressure differential. Such designs include the Fleisch pneumotach, in which the restriction is comprised of many small tubes or a fine screen to ensure laminar flow and a more linear response to flow. Another physical configuration is a flow restriction having an orifice that varies in relation to the flow. However, many known differential pressure flow sensors suffer various deficiencies, depending on the application.

SUMMARY OF THE INVENTION

Accordingly, it is an object of the present invention to provide an airway adapter that overcomes the shortcomings of conventional monitoring systems. This object is achieved according to one embodiment of the present invention by providing an airway adapter that includes a housing, a flow restriction, and a pressure transducer. The housing comprises a flow path, a first pressure port that communicates with the flow path, and a second pressure port that communicates with the flow path. The first pressure port is spaced apart from the second pressure port. The flow restriction is disposed in the flow path between the first and second pressure ports that creates a pressure differential therebetween. The pressure transducer generates a signal that reflects the differential pressure created by the flow restriction between the first and second pressure ports, wherein the pressure transducer comprises an optical interferometer.

Another aspect of the invention relates to an airway adapter comprising a housing, a pressure transducer, and a channel. The housing comprises a flow path, a first pressure port that communicates with the flow path, and a second pressure port that communicates with the flow path. The first pressure port is spaced apart from the second pressure port. The pressure transducer generates a signal that reflects a pressure differential created between the first pressure port and the second pressure port. The channel is formed within the housing that communicates the first pressure port with the second pressure port. A diaphragm of the pressure transducer is disposed within the housing, and the channel is formed proximate to an outer surface of the flow path.

Another aspect of the invention relates to a method of manufacturing an interferometer. The method comprises coating a substrate with a first layer of a first material, the first layer being at least partially transmissive and at least partially reflective for electromagnetic radiation within a wavelength range, coating the first layer with a layer of photoresist; coating the layer of photoresist with a second layer of a second material; the second layer being substantially reflective for electromagnetic radiation with the wavelength range; exposing the photoresist to patterned electromagnetic radiation within the wavelength range; wherein the photoresist exposed to radiation is developed to form one or more spacers; and removing undeveloped photoresist to create a space between the first and second layers.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
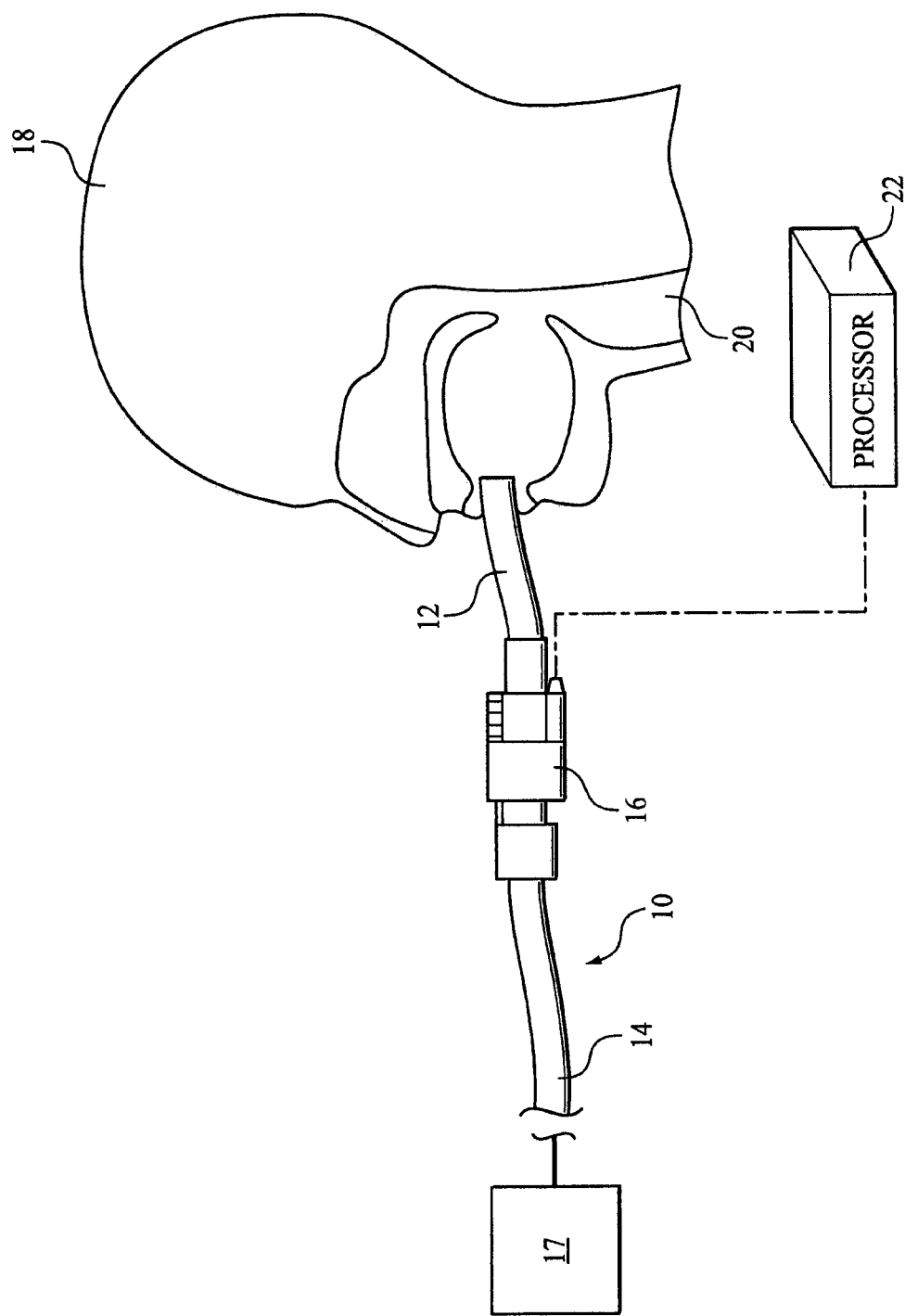
FIG. 1 illustrates a respiratory circuit including an airway adaptor carrying sensors operatively coupled to a processor, in accordance with one embodiment of the invention.

In FIG. 1 a portion of a respiratory circuit 10 is illustrated according to one embodiment of the invention. Respiratory circuit 10 includes a first end 12, a second end 14, and an airway adaptor 16. Respiratory circuit 10 is adapted to deliver a flow of gas to a patient 18. For example, first end 12 of respiratory circuit 10 includes a patient interface appliance configured to communicate with an airway 20 of patient 18. Some examples of the patient interface appliance may include, for example, an endotracheal tube, a nasal canula, a tracheotomy tube, a mask, or other patient interface appliances. Second end 14 of respiratory circuit 10 is configured to communicate with a source of gas 17. For instance, the source of gas may include ambient atmosphere, a wall gas, a pressure support device, a ventilator, or other sources of gas.

As is shown in FIG. 1, airway adaptor 16 is disposed along the length of respiratory circuit 10. Airway adaptor 16 includes one or more sensors that monitor one or more characteristics of the flow of gas provided to patient 18 via respiratory circuit 10 and/or other variables, such as ambient conditions. The sensors are operatively linked to a processor 22. The operative link may include, for instance, a wireless link, a wired link, a link via a network, and/or other communication links.

Each sensor in airway adaptor 16 generates one or more signals that reflect the being monitored by that particular sensor. For example, the one or more signals generated by a given sensor may reflect one or more characteristics of the flow of gas, an ambient condition (e.g., pressure, temperature, humidity, etc.), or another variable. The one or more signals generated by the sensor are transmitted to processor 22 via the operative link between that sensor and processor 22. In one embodiment, the one or more characteristics of the flow of gas that are monitored by the sensor(s) include a pressure (or pressures) of the flow of gas within respiratory circuit 10 at one or more locations, a flow rate of the flow of gas within respiratory circuit 10, a concentration (or concentrations) of one or more gases within the flow of gas, any combination thereof, and/or other characteristics.

In the illustrated embodiment, processor 22 and gas source 17 are shown as separate devices. It is to be understood, however, that the present invention also contemplates that these devices may be incorporated into a common structure.

Figure 2:
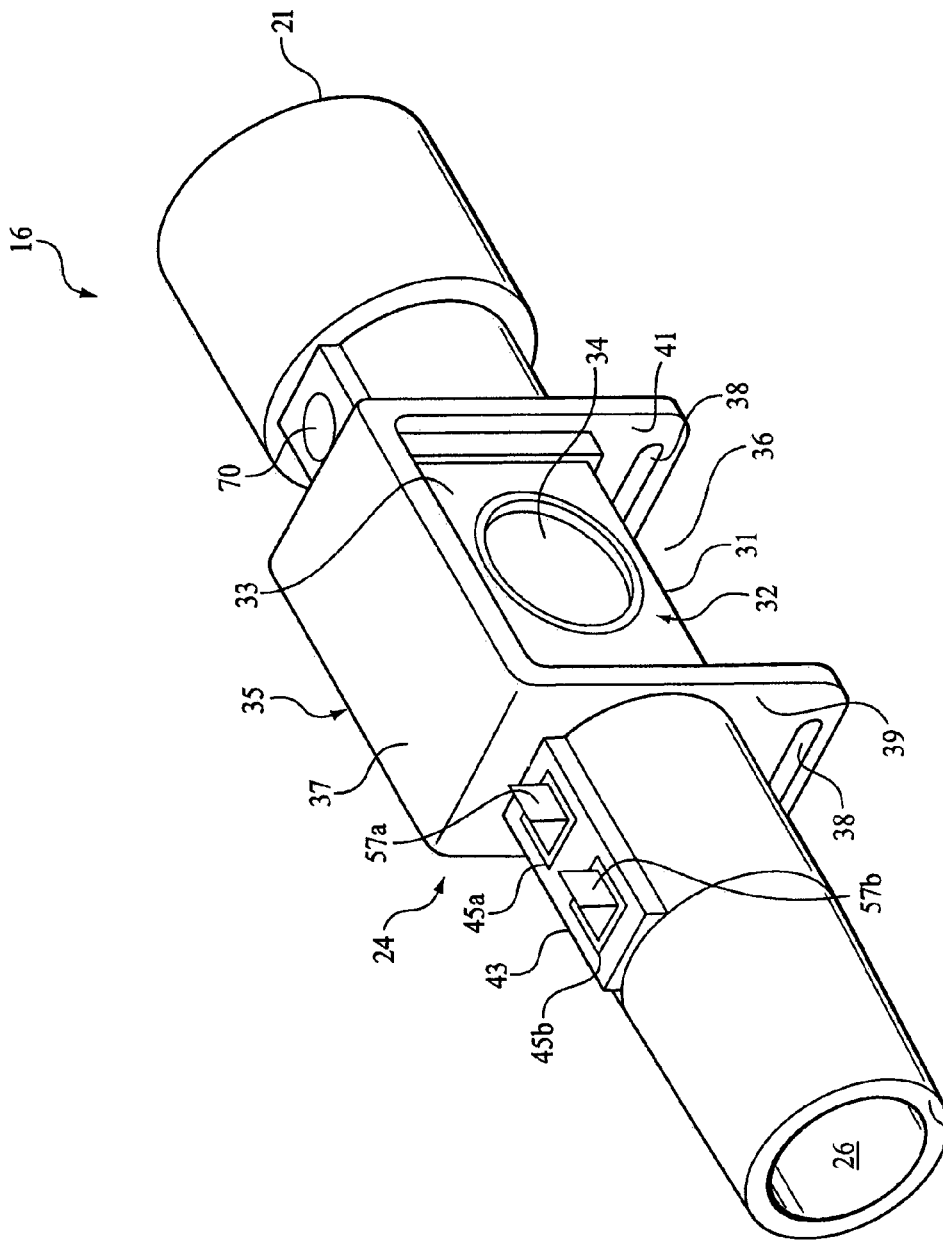
FIG. 2 illustrates a housing of an airway adaptor, according to one embodiment of the invention.

FIG. 2 shows a perspective view of a housing 24 of airway adaptor 16 according to one embodiment of the present invention. Housing 24 provides a flow path 26 from a first end 28 of housing 24 to a second end 30 of housing 24. First and second ends 28 and 30 of housing 24 are generally tubular, and in one embodiment cylindrical, and are configured to be connected with respiratory circuit 10 such that the flow of gas provided to patient 18 via the respiratory circuit passes through or is carried by flow path 26. In one embodiment, one or both of first and second ends 28 and 30 are removably connected with respiratory circuit 10, but in another embodiment are integrally formed with the adjacent tubing. Housing 24 may be composed of a relatively rigid material, for example, housing 24 may composed of polycarbonate and/or PVC.

A detection chamber 32 is provided by housing 24 disposed in flow path 26 between first and second ends 28 and 30. Chamber 32 is bounded on a first side by a wall 31, and on a second and third side by opposing walls 33 and 35. Walls 31, 33, and have substantially planar outer surfaces. A wall 37 bounds housing 24 on a side of chamber 32 opposite from wall 31. Wall 37 protrudes outwardly from housing 24 at the junctions between wall 37 and walls 33 and 35. Chamber 32 is formed such that the flow of gas passing through flow path 26 passes through chamber 32.

Chamber 32 comprises a pair of opposing transmissive windows 34 (only one window being visible in FIG. 2) formed in each of walls 33 and 35. Transmissive windows 34 comprise a material at least partially transmissive for a range of wavelengths. As contemplated herein, in one embodiment, the range of wavelengths can be very small (e.g., only a single wavelength), or in another embodiment, there can be a broad spectrum of wavelengths for which the material is partially transmissive. For example, the selected wavelength(s) may be determined to enable a beam of electromagnetic radiation of the selected wavelength(s) to enter and/or exit chamber 32 so that the selected beam of electromagnetic radiation can be used to determine a concentration (or concentrations) of one or more gases in the flow of gas being provided along flow path 26, as will be discussed further below. In one embodiment, transmissive windows 34 may be formed from sapphire and/or polyethylene.

In the illustrated embodiment, an optical path is provided through chamber 32 via windows 34, so that a constituent of the gas in the chamber, such as the carbon dioxide ($CO_2$), can be measured using well known techniques. The present invention also contemplates providing a single light transmissive window, for example on one side of chamber 32, and measuring a constituent of the gas in the chamber using well known reflectance techniques by directing radiation and detecting radiation reflected back out the same window. The present invention even further contemplates measuring a constituent of the gas in the chamber using a luminescence quenching technique. Of course, more than one gas measurement technique can also be used in combination to measure the gas or gasses in the chamber.

As is illustrated in FIG. 2, the protrusion of wall 37 outward from housing 24, in conjunction with a pair of planar, ridge-like protrusions 39 and 41, defines a seat 36. Protrusions 39 and 41 are formed generally perpendicular to wall 37 such that protrusions 39 and 41 and the protrusions formed by wall 37 frame walls 33 and 35 on three sides. Seat 36 provides a seat for a sensor housing (not shown in FIG. 2) that can be removably docked with housing 24. Protrusions 39 and 41 form a pair of tabs on opposing sides of chamber 32 with a slot 38 formed in each of the tabs. The tabs formed by protrusions 39 and 41 and slots 38 are provided to create a releasable locking mechanism to releasably engage the sensor housing as it is seated in seat 36. As will be described below, the sensor housing may house components of one or more of the sensors included in airway adaptor 16 for monitoring one or more characteristics of the flow of gas through flow path 26, one or more ambient conditions, or other variables.

Housing 24 includes a sensor element seating portion 43 that seats sensor elements 45a and 45b. As will be discussed below, sensor elements 45a and 45b enable the sensors to monitor one or more characteristics of the flow of gas through flow path 26 and/or one or more ambient conditions by observing sensor elements 45a and 45b themselves.

Figure 3A:
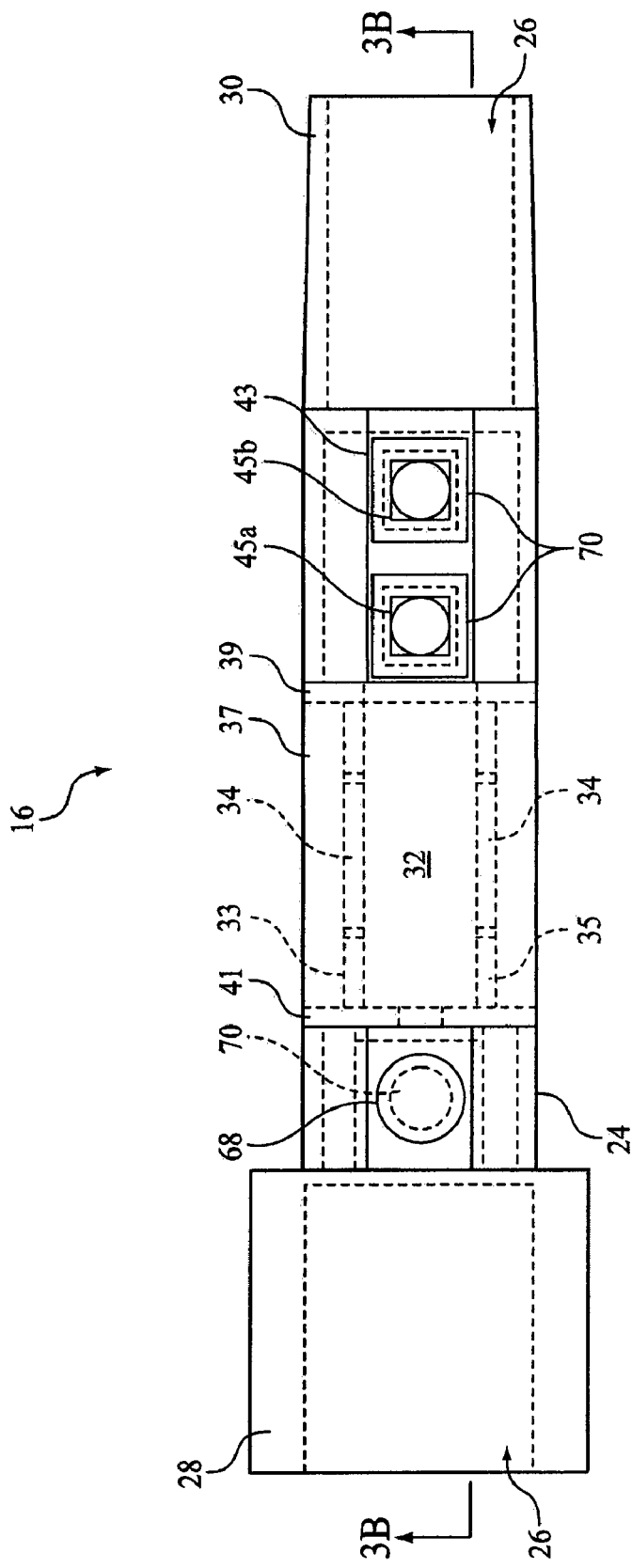
FIG. 3A is a plan view of the airway adapted of FIG. 2.
Figure 3B:
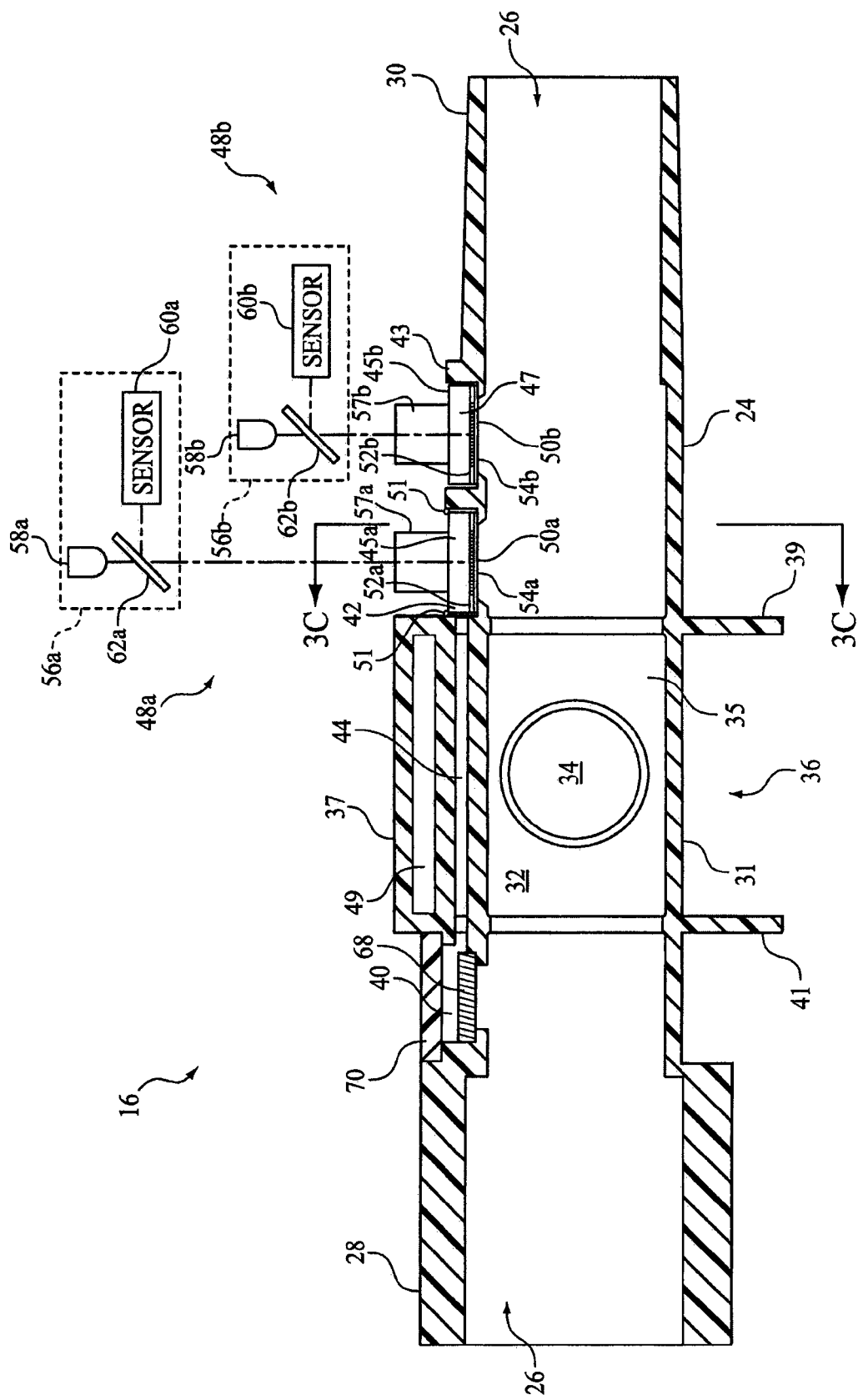
FIG. 3B is a cross-sectional view of a housing of the airway adaptor of FIG. 3A, taken along lines 3B-3B in FIG. 3A.

FIG. 3A is an elevational view of housing 24 (taken from above with respect to the perspective view of FIG. 2). FIG. 3A illustrates the relationship of the features of housing 24 discussed above with respect with FIG. 2. FIG. 3B is a sectional view of housing 24 taken along section line 3B-3B shown in FIG. 3A. Referring to FIG. 3B, housing 24 is adapted to provide access to the flow of gas for one or more of the sensors included in airway adaptor 16. In addition to flow path 26 and chamber 32, housing 24 provides a first pressure port 40 that communicates with flow path 26, a second pressure port 42 that also communicates with flow path 26, and a channel 44 that runs from first pressure port 40 to second pressure port 42. A third pressure port 47 is provided by housing 24 proximate to second pressure port 42. In fact, second and third pressure ports 42 and 47 are provided in housing 24 at sensor element seating portion 43 such that sensor elements 45a and 45b are seated in second and third pressure ports, respectively.

In the embodiment shown in FIG. 3B, an empty space 49 is formed in housing 24 between channel 44 and wall 37. As can be seen in FIG. 3B, flow path 26, first pressure port 40, second pressure port 42, third pressure port 47, channel 44, and detection chamber 32 are all formed within housing 24; and it can be appreciated that, in one embodiment, a plurality (two or more), or even all of these structures can be integrally molded, for example, from a plastic material. In one particular embodiment, channel 44 is integrally molded as part of housing 24.

As illustrated in FIG. 3B, first and second ends 28 and 30 of flow path 26 are configured to be connected with respiratory circuit 10 such that the flow of gas provided to patient 18 by respiratory circuit 10 passes through flow path 26. In one embodiment, one or both of first and second ends 28 and 30 are removably connected with respiratory circuit 10.

As is shown in the embodiment of FIG. 3B, a pair of pressure transducers 48a and 48b are provided to monitor pressures related to the provision of the flow of gas through flow path 26. More particularly, in the illustrated embodiment, the pressures monitored by pressure transducers 48a and 48b include the pressure differential created by the changes in the cross section of flow path 26 between first pressure port 40 and second pressure port 42, and the pressure differential between the flow path and ambient atmosphere. Pressure transducer 48a is configured and arranged to monitor a pressure differential experienced between gas present within flow path 26 at first end 28 (e.g., at first pressure port 40) and gas present within flow path 26 at second end 30 (e.g., at second pressure port 42). Pressure transducer 48b is configured and arranged to monitor a pressure differential experienced between gas present within flow path 26 and an ambient pressure.

In the illustrated embodiment, each of pressure transducers 48a and 48b comprise optical sections (illustrated as optical sections 56a and 56b) and sensor elements (sensor elements 45a and 45b). Sensor element 45a includes a diaphragm 50a that is disposed in communication with channel 44 to substantially seal channel 44 from flow path 26 at second pressure port 42, so that a pressure differential is created between a first side 52a of diaphragm 50a and a second side 54a of diaphragm 50a. A sealing member 51 is disposed about sensor element 45a to seal second pressure port 42 from ambient atmosphere. It should be appreciated that the pressure differential between first side 52a of diaphragm 50a and second side 54a of diaphragm 50a is substantially equivalent to the pressure differential between first pressure port 40a and second pressure port 42a. Diaphragm 50a is formed such that the pressure differential between first side 52a and second side 54a of diaphragm 50a causes diaphragm 50a to deform. This deformation is mathematically related to the pressure differential that causes it.

Similarly, sensor component 45b includes a diaphragm 50b that is disposed in communication with flow path 26 and ambient atmosphere so that a pressure differential is created between a first side of 52b of diaphragm of 50b and a second side 54b of diaphragm 50b. The pressure differential between first side 52b of diaphragm of 50b and second side 54b of diaphragm 50b is the difference in pressure between the gas within flow path 26 and ambient atmosphere. The pressure differential between first side 52b and second side 54b causes diaphragm 50b to deform by a distance that is mathematically related to the magnitude of the pressure differential. In one embodiment, diaphragm 50a and/or diaphragm 50b forms a portion of a boundary of the flow path 26.

To enable the pressure differentials between (i) first pressure port 40 and second pressure port 42, and (ii) flow path 26 and ambient atmosphere to be monitored, pressure transducers 48a and 48b measure the deformation in diaphragms 50a and 50b. In the embodiments shown, pressure transducers 48a and 48b include optical pressure transducers that comprise optical sections 56a and 56b which optically measure the deformations in diaphragms 50a and 50b, respectively.

In one such embodiment, as shown in FIG. 3B, optical section 56a comprises a source 58a and a sensor 60a. Source 58a emits a beam of electromagnetic radiation that will be incident on, and will be reflected by, diaphragm 50a. Sensor element 48a includes a reflective prism 57a that guides the beam of electromagnetic radiation emitted by source 58a to diaphragm 50a. In one embodiment, source 58a may include a light emitting diode ("LED"), a laser, an incandescent source, or another radiation source. The reflected beam of electromagnetic radiation is then guided by prism 57a to become incident on a beam splitter 62a included in optical section 56a that directs the beam of electromagnetic radiation to sensor 60a. In some instances, optical section 56a may include a member disposed in the optical path of the beam of electromagnetic radiation to reduce noise in the form of ambient and/or reflected radiation that will be incident on sensor 60a.

Based on one or more aspects of the electromagnetic radiation incident on sensor 60a, the deformation of diaphragm 50a can be determined. In some instances, sensor 60a generates one or more signals that reflect the one or more aspects of the electromagnetic radiation that are indicative of the deformation of diaphragm 50a. For example, the one or more aspects of the electromagnetic radiation may include an intensity, a phase, a frequency, a frequency shift, or other aspects. The one or more signals generated by sensor 60a are transmitted to processor 22 via the operative link between the sensors in airway adaptor 16 and processor 22. Optical section 56b includes a source 58b, a sensor 60b, and a beam splitter 62b that operate similarly to the components of optical section 56a. As can be seen in FIG. 3B, sensor element 45b includes a reflective prism 57b that guides electromagnetic radiation to and from diaphragm 50b similar to reflective prism 57a.

In the embodiment of FIG. 3B, sensor elements 45a and 45b receive electromagnetic radiation directly through prisms 57a and 57b. In other embodiments (not shown), housing 24 encloses sensor elements 45a and 45b and includes one or more transmissive windows through which the beams of electromagnetic radiation are transmitted to and from sensor elements 45a and 45b. In other embodiments (not shown), some of all of the components of optical sections 56a and 56b may be provided within housing 24. It should also be appreciated that the position of diaphragm 50a with respect to channel 44 is not intended to be limiting, and that alternative configurations of diaphragm 50a and channel 44 may be employed without departing from the teachings of this disclosure. For example, diaphragm 50a may be disposed at first pressure port 40 instead of at second pressure port 42, or diaphragm 50a may be disposed in channel 44 some distance from each of first and second pressure ports 40 and 42.

To protect channel 44 from humidity (e.g., spittle from patient 18, etc.) a member 68 is disposed at first pressure port 40. In an exemplary embodiment, member 68 is a hydrophobic member that substantially prevents moisture from entering channel 44. Housing 24 includes a plate 70 that can be removed to provide access to member 68. In one embodiment, plate 70 is formed from substantially the same material as the rest of housing 24. In some instances, plate 70 is attached to housing 24, after member 68 is disposed therein, in a substantially permanent manner (e.g., adhesive, ultrasonic welding, etc.). In other instances, plate 70 is removably attached to housing 24 to seal the interior from ambient conditions while still providing periodic access to member 68 for cleaning and/or replacement. Although in FIG. 3B, member 68 is shown disposed at first pressure port 40, in other embodiments, member 68 may be disposed elsewhere within channel 44. In another embodiment, in which diaphragm 50 is located within channel 44 away from both of first and second pressure ports 40 and 42, a member may be placed at each of first and second pressure ports 40 and 42 to prevent the ingress of moisture on channel 44.

Figure 3C:
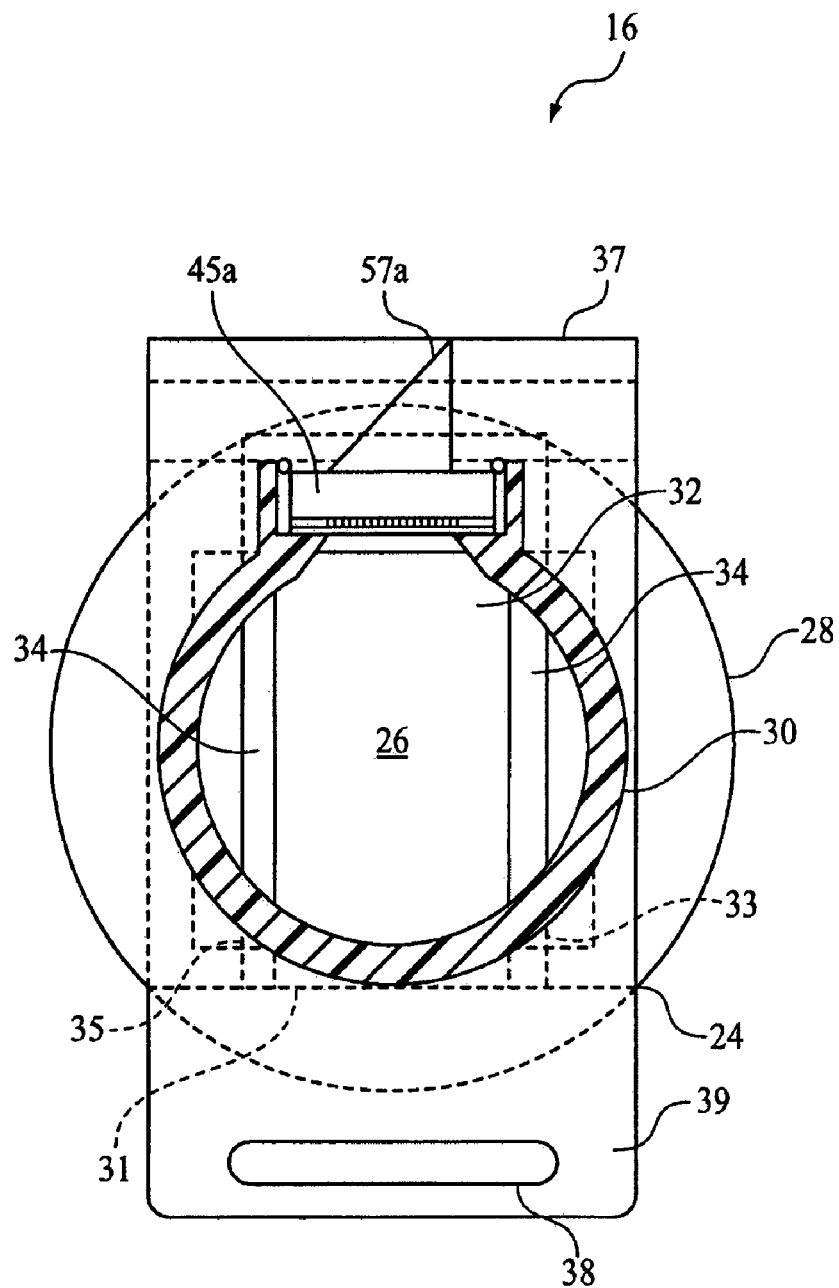
FIG. 3C is a cross-sectional view of the airway adaptor of FIG. 3A, taken along lines 3C-3C in FIG. 3B.

FIG. 3C is a sectional view of housing 24 taken along section line 3C-3C shown in FIG. 3B. It should be appreciated from FIG. 3C that as the flow of gas passes through flow path 26, changes in the cross section of flow path 26 (e.g., from first section 26 to chamber 32, from chamber 32 to second section 30, etc.) act as flow restrictions that create the pressure differential between first pressure port 40 and second pressure port 42. This pressure differential cause by changes in the cross section of flow path 26 is mathematically related to the flow rate of the flow of gas through flow path 26. Thus, from measurements of the pressure differential created by these cross-sectional changes (e.g., the differential pressure between first pressure port 40 and second pressure port 42), the flow rate of the gas through flow path 26 may be calculated.

The present invention contemplates creating a pressure differential between first pressure port 40 and second pressure port 42 using other techniques in addition to or instead of decreasing the cross-sectional area of the gas flow path between these ports. For example, a flow element, such as that disclosed in U.S. Pat. No. 6,915,705, can be provided between first pressure port 40 and second pressure port 42 to create the pressure gradient.

Figure 4:
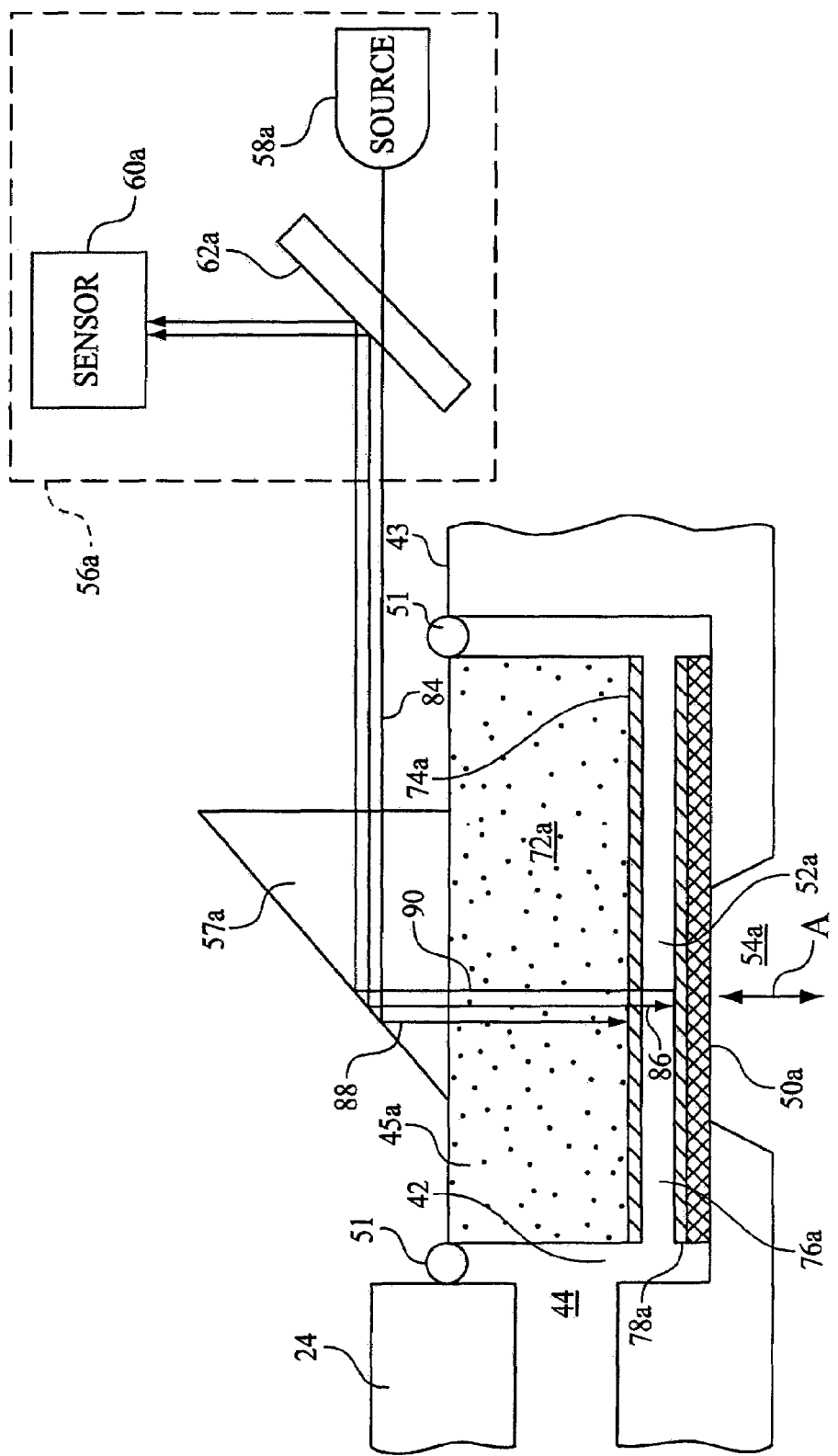
FIG. 4 illustrates an optical pressure transducer, in accordance with one embodiment of the invention.

FIG. 4 illustrates the operation of pressure transducer 48a, according to one embodiment of the invention. As noted above, pressure transducer 48a comprises optical section 56a and sensor element 45a that carries diaphragm 50a. Sensor element 45a comprises a substrate layer 72a, a first reflective layer 74a, a pressure channel 76a, a second reflective layer 78a, and diaphragm 50a. As was described briefly above, the creation of a pressure differential between first side 52a of sensor element 45a and second side 54a of sensor element 45a causes diaphragm 50a to deform as generally indicated by arrow A. Diaphragm 50a deforms in response to a pressure differential between first side 52a and second side 54a because the pressure on first side 52a of sensor element 45a is communicated to diaphragm 50a by pressure channel 76. Pressure channel 76a is created between first reflective layer 74a and second reflective layer 78a by spacers formed by a photoresist layer (not shown in FIG. 4), which supports reflective layers 74a and 78a apart from each other. In one embodiment, pressure transducer 48a basically forms an optical interferometer to optically measure this deformation.

To measure the deformation of diaphragm 50a, source 58a emits a beam 84 of electromagnetic radiation that is guided toward diaphragm 50a by prism 57a. Beam 84 passes through substrate layer 72a (which is substantially transparent to the wavelength range of beam 84) to first reflective layer 74a. First reflective layer 74a is partially reflective (e.g., 40%-60% reflective of the wavelength being used for beam 84), so as beam 84 becomes incident on first reflective layer 74a, a beam 86 of electromagnetic radiation travels through first reflective layer 74a to second reflective layer 78a and a beam 88 of electromagnetic radiation is reflected by first reflective layer 74a back toward prism 57a, which guides beam 88 back to optical section 56a.

As beam 86 becomes incident on second reflective layer 78a (which is substantially 100% reflective to the wavelength of beam 86), a beam 90 of electromagnetic radiation is reflected by second reflective layer 78a back toward prism 57a, which guides beam 90 back to optical section 56a. It should be appreciated that the depiction of beams 84, 86, 88, and 90 in FIG. 4 as being translationally offset from each other is shown schematically for illustrative purposes only, as in actual practice beams 84, 86, 88, and 90 would be coaxial. In FIG. 4 beams 84, 86, 88, and 90 have been illustrated as being offset for convenience in explaining the way in which light is processed by pressure transducer 48a to determine a deformation of diaphragm 50a.

As can be seen in FIG. 4, beams 88 and 90 are deflected by beam splitter 62a toward sensor 60a. Sensor 60a may include any photo sensitive element or array of elements capable of generating one or more signals that reflect one or more characteristics of the electromagnetic radiation in beams 88 and 90 that is incident on sensor 60a. For example, sensor 60a may include one or more photodiodes, a CCD array, a CMOS array, a photomultiplier, or other photo sensitive elements.

As can be seen in FIG. 4, the electromagnetic radiation included in beam 90 travels a longer optical path from source 58a to detector 60a than the electromagnetic radiation included in beam 88. Specifically, since beam 88 comprises radiation that is reflected by first reflective layer 74a, its path length is shorter by 2 times the distance between first reflective layer 74a and second reflective layer 78a than the path length of the radiation included in beam 90, which is reflected by second reflective layer 74a. Due to this difference in path length, the electromagnetic radiation of beams 88 and 90 arrive at sensor 60a with a phase difference. In one embodiment of the invention, this phase difference enables the optical path length differences for the radiation in beams 88 and 90, and/or the distance between first and second reflective layers 74a and 78a to be determined based on the signal(s) generated by sensor 60a. Because substrate layer 72a is substantially rigid, any deformation in diaphragm 50a is included in this measurement of the distance between first and second reflecting layers 74a and 78a.

It will be recognized from the above description that the interferometer formed by pressure transducer 48a in one embodiment to measure the deformation of diaphragm 50a is of the Fabry-Perot type. As such, the distance between first and second reflective layers 74a and 78a should be an odd number of ¼ waves of radiation apart, in order to provide a null return (total destructive interference between beams 88 and 90 when there is no deformation of diaphragm 50a). For instance, the distance between first and second reflective layers 74a and 78a may be 1¼ waves total. In one embodiment, an additional ⅛ wave may be added to the distance to bias the return to one half of full amplitude. This would enable the system to differentiate between instances in which diaphragm 50a is not deformed and instances in which an error is causing a reading of zero. Other configurations for spacing first and second reflective layers 74a and 78a may be implemented.

Figure 5:
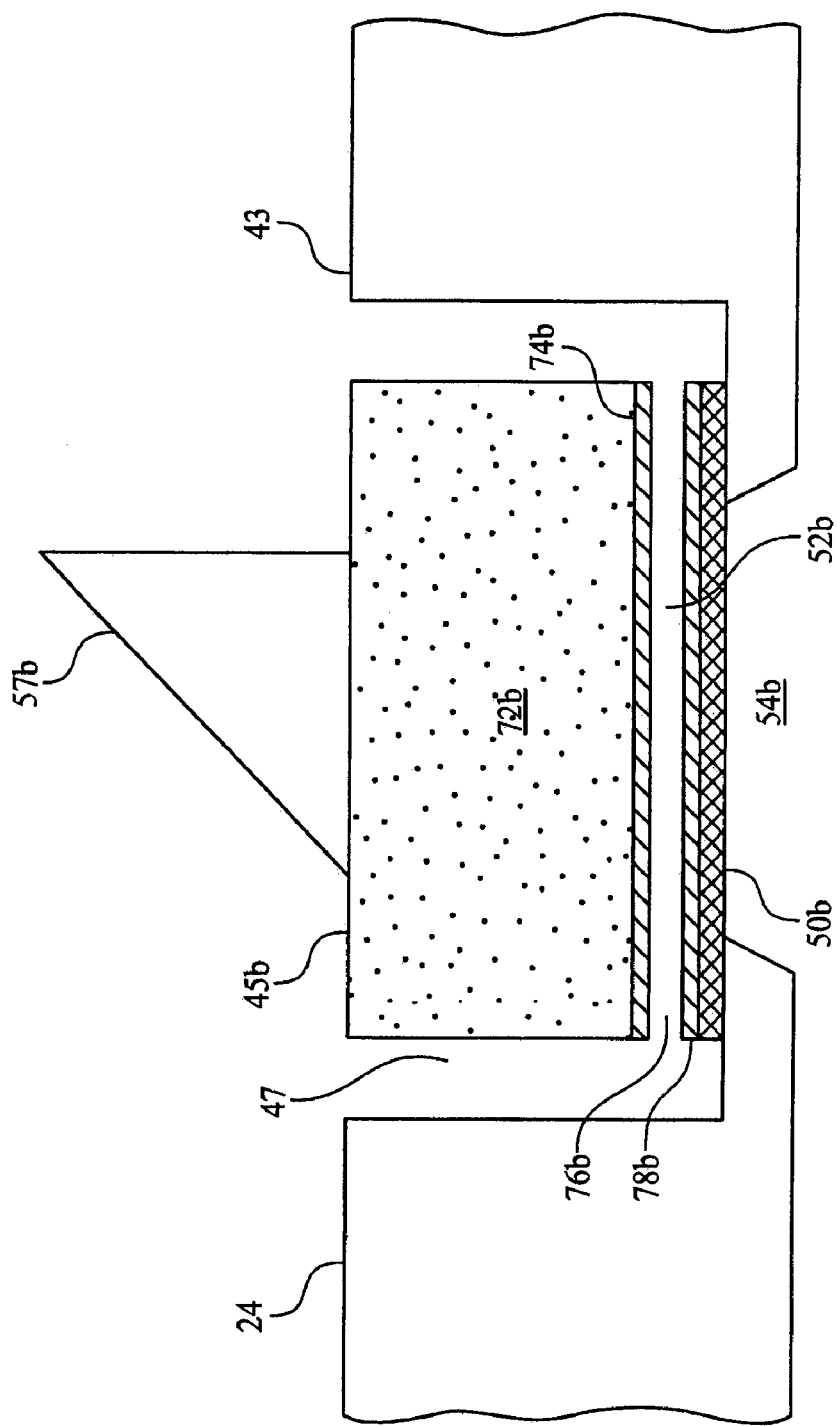
FIG. 5 illustrates a sensor element, according to one embodiment of the invention.

FIG. 5 is a sectional view of pressure transducer 48b, including sensor element 45b seated in sensor element seating portion 43. Sensor element 45b includes components that correspond substantially to the components of sensor element 45a. For example, sensor element 45b includes a substrate layer 72b, a first reflective layer 74b, a second reflective layer 78b, a pressure channel 76b, and diaphragm 50b. As can be seen, sensor element 45b is seated in sensor element seating portion 43 such that pressure channel 76b communicates with ambient atmosphere. Therefore, the pressure differential present at diaphragm 50b that cause deformation of diaphragm 50b is the pressure difference between the gas in flow path 26 at third pressure port 47 and ambient atmosphere. This pressure differential may be used to determine, among other things, the barometric pressure of the gas within flow path 26.

Although not illustrated in FIG. 5, it should be appreciated that the components of sensor element 45b function with the components of optical section 56b to determine the deformation of diaphragm 50b in a manner substantially identical to the one one described above with respect to the determination of deformation in diaphragm 50a by the components of sensor element 45a and optical section 56a.

Optionally, housing 24 of airway adapter 16 may be coupled with a sensor housing configured to carry one or more sensors that provide diagnostic functions. By way of example only, in addition to functioning as a flow sensor and/or a barometric pressure gauge using pressure transducers 48a and/or 48b, an airway adapter of the present invention may also include a material sensing element, such as one or both of an infrared sensor, as described in the U.S. Pat. Nos. 4,859,858 and 4,859,859, both of which issued to Knodle et al. on Aug. 22, 1989 (hereinafter respectively "the '858 patent" and "the '859 patent"), and U.S. Pat. No. 5,153,436, issued to Apperson et al. on Oct. 6, 1992 (hereinafter "the '436 patent"), the disclosures of each of which are hereby incorporated by this reference in their entireties, and a luminescence quenching type sensor, as described in U.S. Pat. No. 6,325,978, issued to Labuda et al. on Dec. 4, 2001 (hereinafter "the '978 patent"), the disclosure of which is hereby incorporated herein by this reference in its entirety. The sensor housing may incorporate some or all of the features of the sensor housing(s) disclosed in U.S. Pat. No. 5,693,944, issued to Rich on Dec. 2, 1997 (herinafter "the '944 patent"), the contents of which are incorporated herein by reference.

Figure 6:
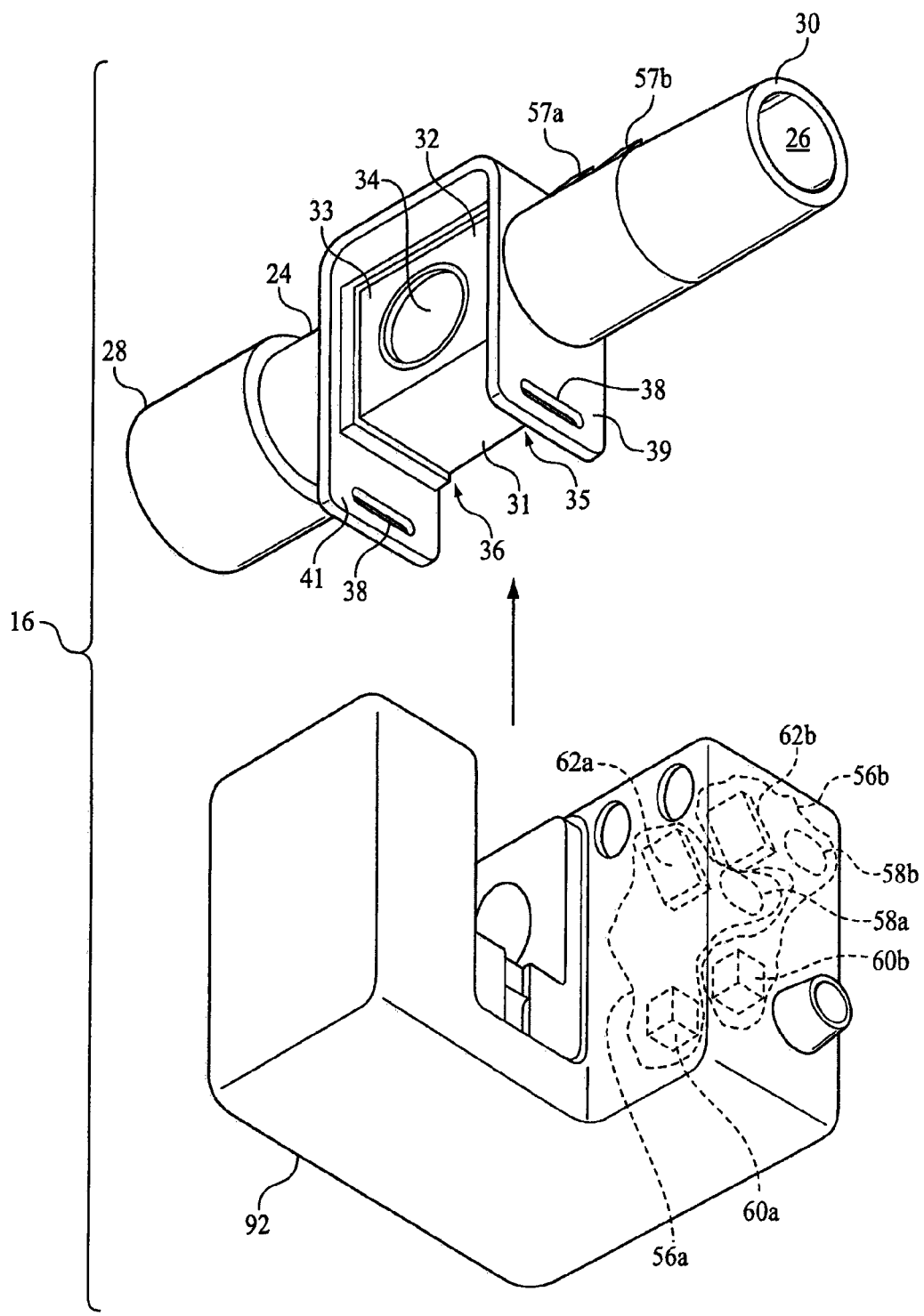
FIG. 6 illustrates a housing and a sensor housing of an airway adaptor, according to one embodiment of the invention.

FIG. 6 is a perspective view of an example of a multi-function airway adapter 16 including housing 24 that is configured to receive and a sensor housing 92 that includes an infrared type sensor that may be used therewith. Housing 24 has the features described previously herein with reference to FIGS. 3 and 4. As can be seen, optical sections 56a and 56b are carried within sensor housing 92 such that optical sections 56a and 56b are optically coupled with sensor elements 45a and 45b when sensor housing 92 is seated at seat 36.

As was mentioned briefly above, seat 36 of housing 24 is configured to ensure that the complementarily configured sensor housing 92 seats properly, i.e., in the proper orientation, when housing 24 and sensor housing 92 are assembled with one another. Sensor housing 92 includes the elements of an infrared monitoring transducer, for example as described in the '858, '859, and '436 patents.

Figure 7:
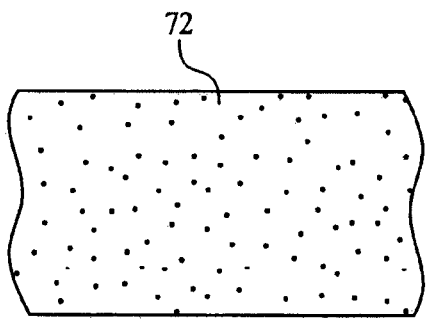
FIG. 7 illustrates a step in a method of manufacturing a sensor component, in accordance with one embodiment of the invention.

FIGS. 7-17 illustrate a method of manufacturing a sensor element 45. FIG. 7 shows substrate layer 72 at one step in the method. Substrate layer 72 may form the base from which sensor element 45 is manufactured. As was mentioned previously, substrate layer 72 is substantially transparent. For example, substrate layer may be formed from glass, silica, and/or a transparent plastic (e.g., acrylic). At the depicted step in the method, substrate layer 72 may be between about 2 mm thick and about 4 mm thick. A side of substrate layer 72, on which first reflecting layer 74 will be deposited, is smoothed with a predetermined degree of precision. In one embodiment, the smoothed side of substrate layer 72 must be smoothed to within one tenth (1/10) of a wavelength of the radiation emitted by one or both of source 58a and source 58b.

Any process capable of providing the requisite smoothness may be implemented. For example, rolling, calendaring, and/or spin-casting may be used. In one embodiment, not shown in FIGS. 7-17, a side of substrate layer 72 opposite the smoothed side is formed at an angle to smoothed side. This will reduce interference within pressure transducer 48 caused by reflections of radiation at the angled side of substrate layer 72 during operation. In one embodiment, the side opposite the smoothed side is also smoothed for optical processing purposes. In some instances, the smoothing may be done using the same method used to smoothed the "smoothed side." This opposing surfaces may even be smoothed simultaneously.

Figure 8:
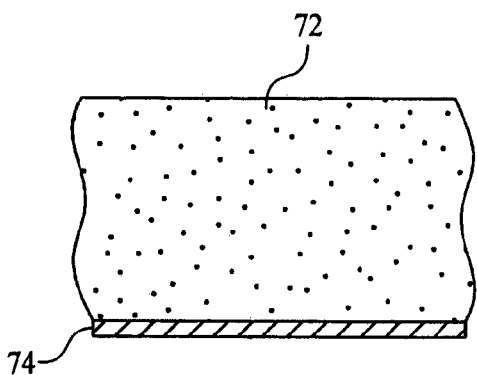
FIG. 8 illustrates a step in a method of manufacturing a sensor component, in accordance with one embodiment of the invention.

FIG. 8 illustrates substrate layer 72 with first reflective layer 74 disposed on the smooth side of substrate layer 72. First reflective layer 74 may comprise any reflective material capable of being applied with a predetermined uniformity to substrate layer 72. In one embodiment, first reflective layer 74 includes chromium, or aluminum. The predetermined uniformity includes, in one embodiment, a smoothness of 1/10 of a wavelength of the radiation emitted by one or both of source 58a and source 58b.

Figure 9:
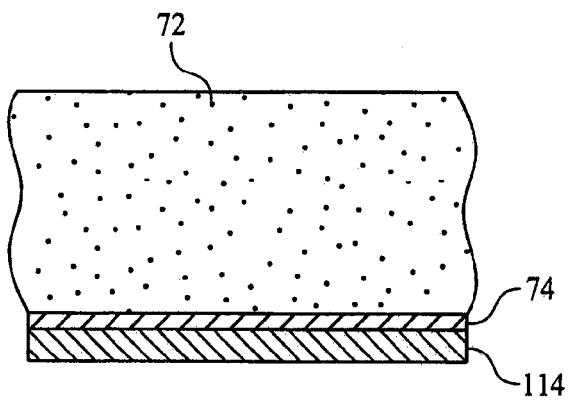
FIG. 9 illustrates a step in a method of manufacturing a sensor component, in accordance with one embodiment of the invention.

Subsequent to the deposition of first reflective layer 74 on substrate layer 72, a layer of photoresist 114 is deposited on first reflective layer 74, as is illustrated in FIG. 9. The thickness of layer of photoresist 114 dictates the distance between first and second reflective layers 74 and 78. Consequently, in one embodiment, the thickness of layer of photoresist 114 is equal to an odd number of 1/4 wavelengths of the radiation emitted by one or both of sources 58a and 58b. In some instances, an additional 1/8 wavelength may be added to the thickness for the reasons presented above. As with the layers previously discussed, layer of photoresist 114 may be deposited with a predetermined uniformity and precision. For example, spin-coating or vapor deposition may be used to deposit photoresist with a uniformity and precision of 1/10 of a wavelength of the radiation emitted by one or both of source 58a and 58b.

Figure 10:
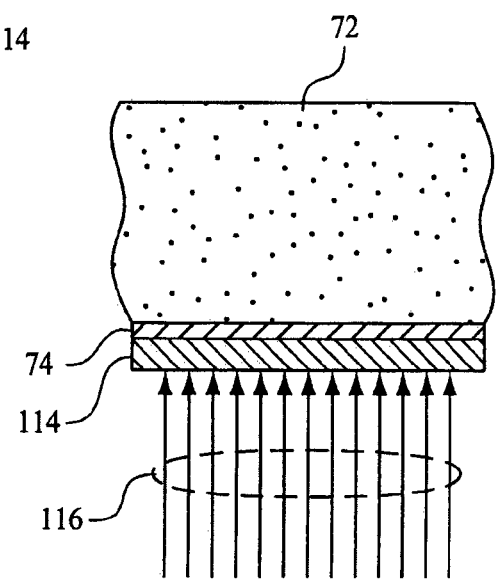
FIG. 10 illustrates a step in a method of manufacturing a sensor component, in accordance with one embodiment of the invention.

FIG. 10 illustrates the exposure of layer of photoresist 114 to electromagnetic radiation 116. Photoresist exposed to electromagnetic radiation 116 can be developed to form the spacers that will eventually support first reflective layer 74 apart from second reflective layer, thereby forming pressure channel 76. It should be appreciated that although FIG. 10 illustrates electromagnetic radiation 116 becoming incident on layer of photoresist 114 on a side of layer of photoresist that is open to atmosphere, layer of photoresist 114 could instead (or also) be exposed to electromagnetic radiation from the side of layer of photoresist 114 opposite the side illustrated in FIG. 10, through substrate layer 72 and first reflective layer 74.

Figure 11:
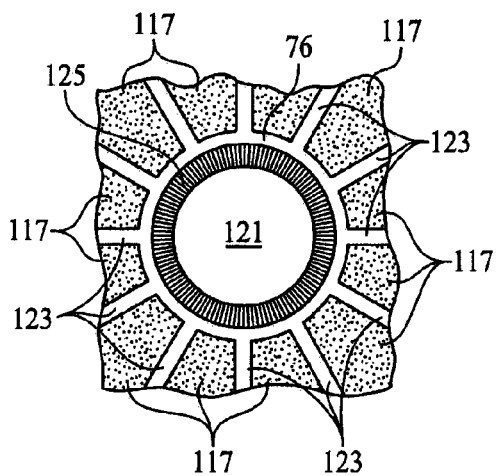
FIG. 11 illustrates a step in a method of manufacturing a sensor component, in accordance with one embodiment of the invention.

Electromagnetic radiation 116 is patterned prior to being directed onto layer of photoresist 114 to ensure that the photoresist that becomes hardened by electromagnetic radiation 116 will form one or more spacers with a predetermined structure. For example, FIG. 11 illustrates an exposure pattern of electromagnetic radiation 116. In the exposure pattern of FIG. 11, electromagnetic radiation 116 is directed onto layer of photoresist 114 to form a plurality of spacers 117 that define the shape of pressure channel 76. Undeveloped photoresist (the areas of layer of photoresist 114 not receiving electromagnetic radiation) is cleared to form pressure channel 76. In the illustrated embodiment, pressure channel 76 includes a central region 121 with a plurality of inlets 123 that communicate central region 121 with the periphery. The exposure pattern further cause a plurality of ridges 125 to be formed in central region 121.

Figure 12:
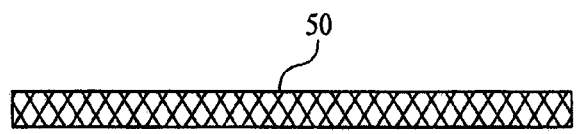
FIG. 12 illustrates a step in a method of manufacturing a sensor component, in accordance with one embodiment of the invention.

FIG. 12 illustrates diaphragm 50. Diaphragm 50 is flexible, to allow for deformation during operation, and thin. In one embodiment, diaphragm 50 is in the range of 1-3 thousandths of an inch in thickness and is composed of a plastic (e.g., SU-8), silicon, silicon-nitride, glass, or metal (e.g., nickel). Diaphragm 50 may be formed with a predetermined uniformity.

Figure 13:
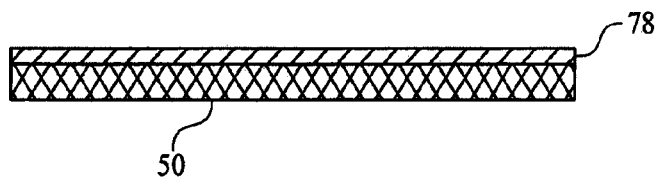
FIG. 13 illustrates a step in a method of manufacturing a sensor component, in accordance with one embodiment of the invention.

FIG. 13 illustrates a step in the method wherein second reflective layer 78 is disposed on diaphragm 50. Second reflective layer 78 may comprise any reflective material capable of being applied with a predetermined uniformity to layer of diaphragm 50. In one embodiment, second reflective layer 78 includes aluminum, or chromium. The predetermined uniformity includes, in one embodiment, a smoothness of 1/10 of a wavelength of the radiation emitted by sources 58a and/or 58b. In one embodiment (not shown) alternative to the one illustrated here, second reflective layer 78 may be formed first, and then diaphragm 50 may be deposited thereon.

Figure 14:
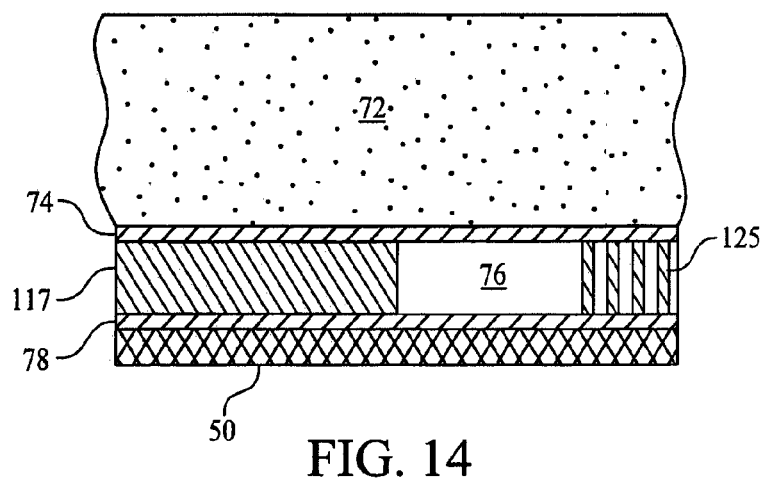
FIG. 14 illustrates a step in a method of manufacturing a sensor component, in accordance with one embodiment of the invention.

FIG. 14 shows substrate layer 72, with first reflective layer 74, and spacers 117 and ridges 125 formed from layer of photoresist 114, joined to diaphragm 50 and second reflective layer 78. This may be accomplished by bonding spacers 117 to second reflective layer 78. In one embodiment, spacers 117 may be bonded to second reflective layer 78 by compressing the surfaces together with sufficient force. To enhance the bond, the opposing surfaces may be kept extremely clean, and/or heat may be provided to the contacting areas of the surfaces. During the bonding process, ridges 125 may keep any compression applied to substrate layer 72 and diaphragm 50 from causing first and second reflective layers 74 and 78 to come into contact.

In one embodiment, not illustrated here, layer of photoresist 114 may be applied to second reflective layer 78 and diaphragm 50 and exposed there to form spacers 117 and/or ridges 125. This amalgam may then be bonded to substrate layer 72 and first reflective layer 74. In another possible embodiment, the exposure pattern used to expose layer of photoresist 114 may not include ridges 125.

Figure 15:
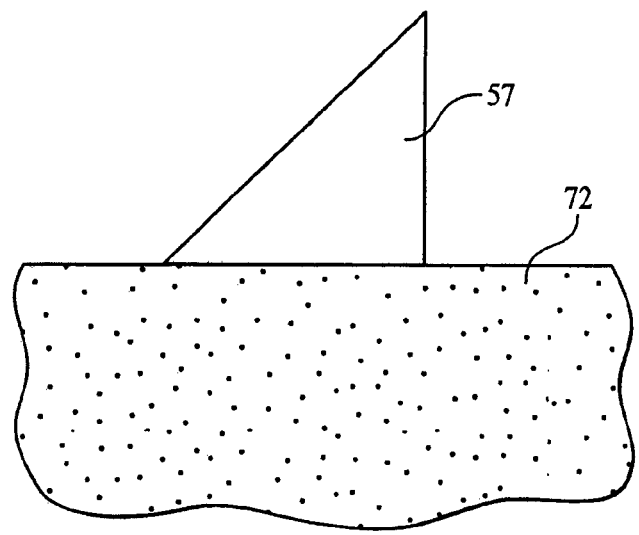
FIG. 15 illustrates a step in a method of manufacturing a sensor component, in accordance with one embodiment of the invention.

FIG. 15 shows prism 57 bonded to substrate layer 72. In one embodiment, prism 57 is bonded to substrate layer 72 using a glue. In some instances, the glue is index matched to one or both of prism 57 and substrate layer 72. Prism 57 is bonded on substrate layer 72 above central region 121.

Figure 16:
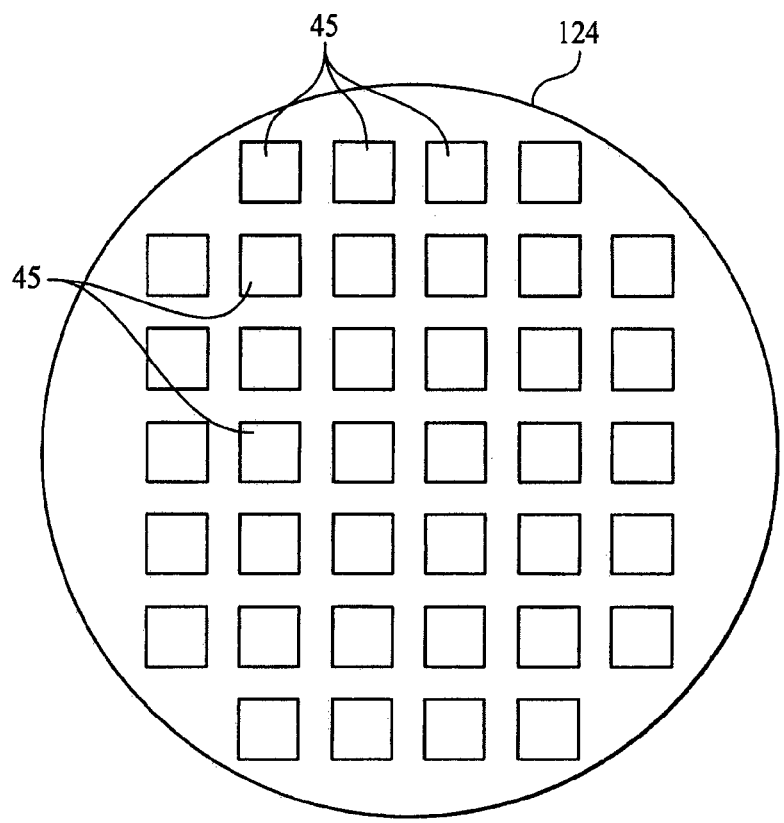
FIG. 16 illustrates a step in a method of manufacturing a sensor component, in accordance with one embodiment of the invention.

In one embodiment, the above described method may be performed using materials (e.g., substrate layer 72, reflective layers 74 and 78, photoresist layer 114, etc.) with dimensions larger than a single sensor element. In this embodiment, a plurality of exposure patterns may be directed onto the materials. The regions of the materials where undeveloped photoresist has been cleared to form pressure channels 76 may then be "cut out" or separated in the appropriate shape to form sensor element 45. For example, FIG. 16 illustrates a single substrate 124 that includes a plurality of sensor elements 45 to be cut out. It should be appreciated that various ones of the above described steps may be performed after the individual sensor elements 45 are separated. For instance, 57 may be bonded to substrate layer 72 after separation.

Figure 17:
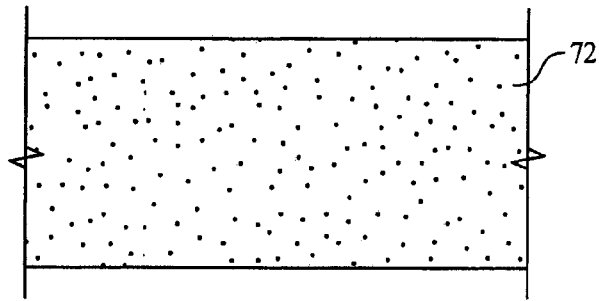
FIG. 17 illustrates a step in a method of manufacturing a sensor component, according to one embodiment of the invention.
Figure 18:
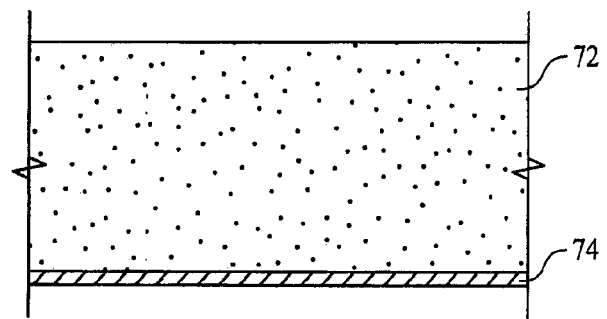
FIG. 18 illustrates a step in a method of manufacturing a sensor component, according to one embodiment of the invention.
Figure 19:
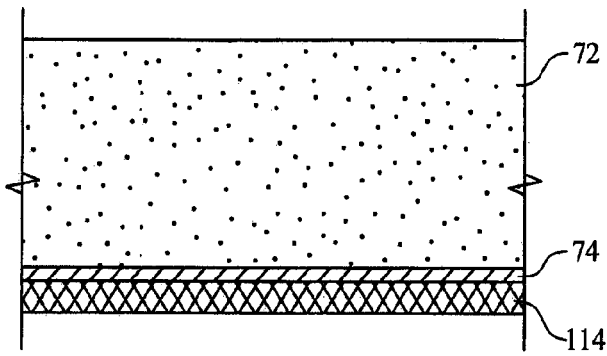
FIG. 19 illustrates a step in a method of manufacturing a sensor component, according to one embodiment of the invention.

FIGS. 17-26 illustrate a method of manufacturing sensor element 45 that includes combining and processing substrate layer 72, reflective layers 74 and 78, photoresist layer 114, and diaphragm 50 to produce sensor element 45. FIG. 17 shows substrate layer 72 at a formative step in the method, prior to combination with the other materials. At a step illustrated by FIG. 18, first reflective layer 74 is disposed on substrate layer 72 similar to the deposition of first reflective layer 74 on substrate layer 72 illustrated above in FIG. 8. FIG. 19 shows a step in the method at which layer of photoresist 114 is deposited on first reflective layer 74, for example, in the manner described above with respect to FIG. 9.

Figure 20:
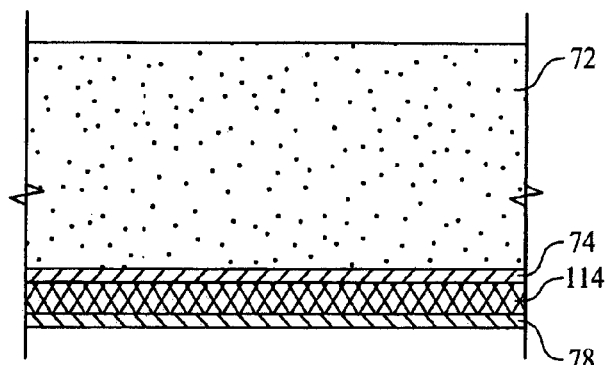
FIG. 20 illustrates a step in a method of manufacturing a sensor component, according to one embodiment of the invention.

FIG. 20 illustrates the step in the method illustrated by FIGS. 17-26 at which the illustrated method diverges from the method illustrated in FIGS. 17-27. In the step shown in FIG. 20, second reflective layer 78 is deposited onto layer of photoresist 114 at a predetermined uniformity. In one embodiment, second reflective layer 78 includes aluminum. The predetermined uniformity includes, in one embodiment, a smoothness of 1/10 of a wavelength of the radiation emitted by one or both of sources source 58a and 58b.

Figure 21:
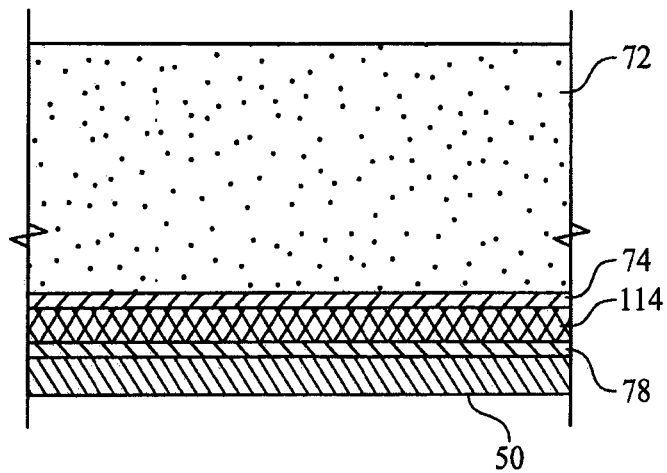
FIG. 21 illustrates a step in a method of manufacturing a sensor component, according to one embodiment of the invention.

FIG. 21 illustrates diaphragm 50 deposited on second reflective layer 78. Diaphragm 50 may be deposited using any method capable of providing diaphragm 50 with a predetermined uniformity. For instance, diaphragm 50 may be spin-coated or vapor deposited on second reflective layer 78.

Figure 22:
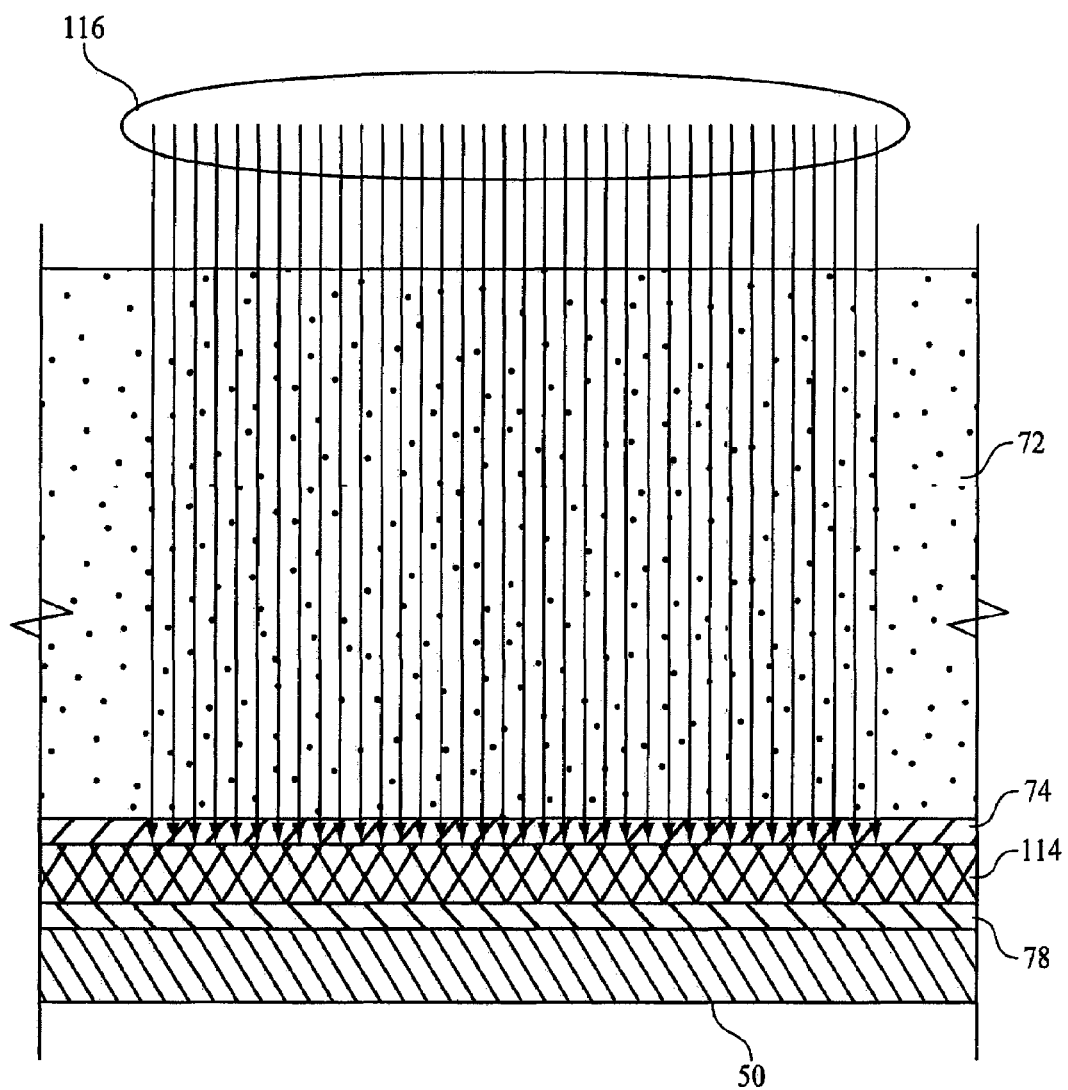
FIG. 22 illustrates a step in a method of manufacturing a sensor component, according to one embodiment of the invention.

FIG. 22 illustrates a step in the manufacturing of sensor element 45 that typically takes place after layers 74, 114, 78, and 50 have been deposited on first side 110 of substrate layer 72. More particularly, patterned electromagnetic radiation 116 is transmitted through substrate layer 72 and first reflective layer 74 onto layer of photoresist 114. Electromagnetic radiation 116 is provided at a wavelength that develops the areas of layer of photoresist 114 on which radiation 116 is incident.

Figure 23:
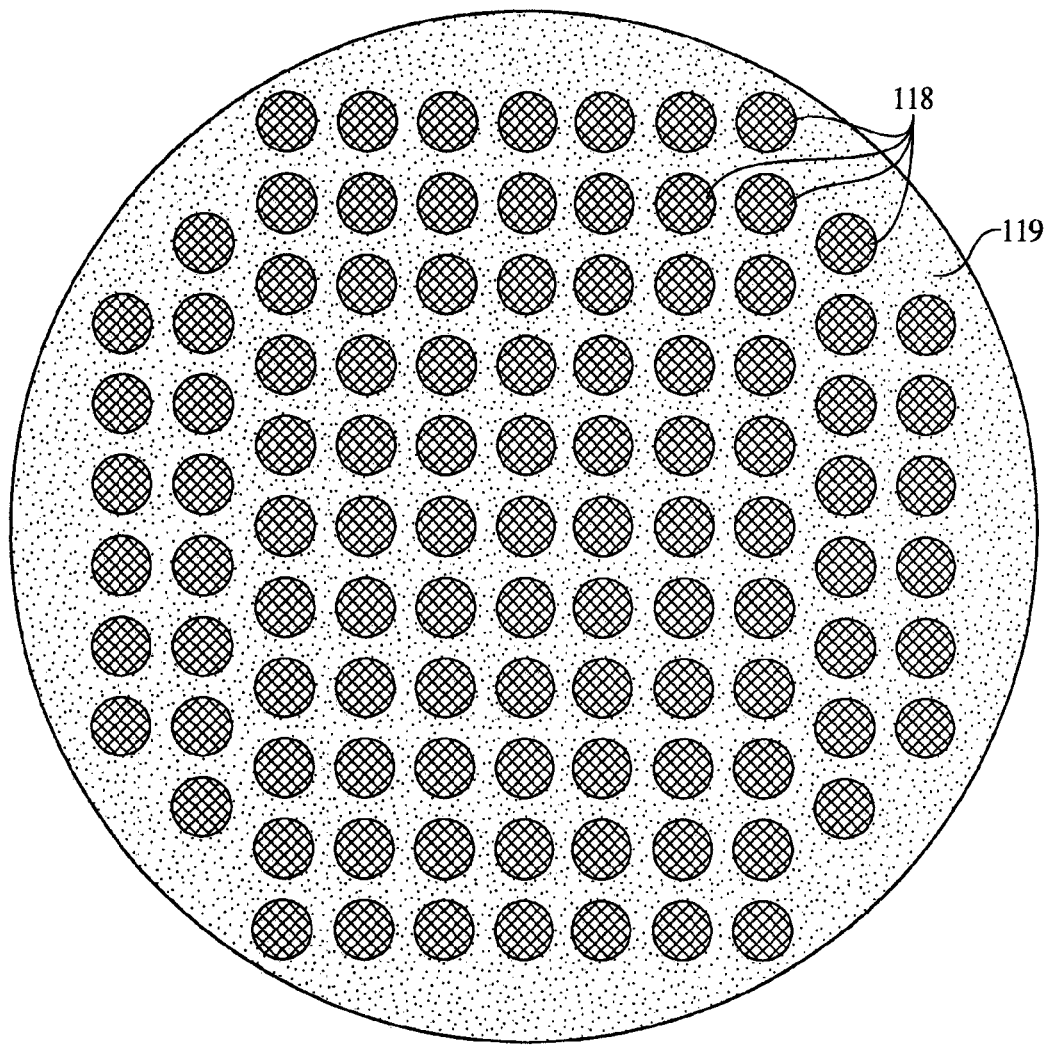
FIG. 23 illustrates a step in a method of manufacturing a sensor component, according to one embodiment of the invention.

In one embodiment of the invention, materials (e.g., substrate layer 72, first and second reflective layers 74 and 78, layer of photoresist 114, and diaphragm 50) have dimensions larger than a single sensor element, and electromagnetic radiation 116 is patterned to expose layer of photoresist 114 in a pre-determined pattern on a plurality of regions of the materials. One such pattern is illustrated in FIG. 23, which shows a plurality of regions 118 of a substrate made up of the materials (shown in FIG. 23 as substrate 119) that have been exposed by electromagnetic radiation 116. Each of the regions 118 may be subsequently processed to form a sensor element (e.g. sensor element 45). Since the layers in the method of FIGS. 17-26 are not bonded together after the formation of pressure channel 76, the patterned electromagnetic radiation may not form ridges (e.g., ridges 125 in FIG. 11), or other support structures in pressure channel 76.

In some instances (not illustrated here), pressure channel 76 includes inlets that extend from the periphery of sensor element 45 to a central region, similar to inlets 123 and central region 121 shown in FIG. 11 and described above. In these instances the individual sensor elements 45 may be separated from substrate 119, and the inlets may be used to clean or flush the undeveloped photoresist out of pressure channel 76, thus removing the undeveloped photoresist.

Figure 24:
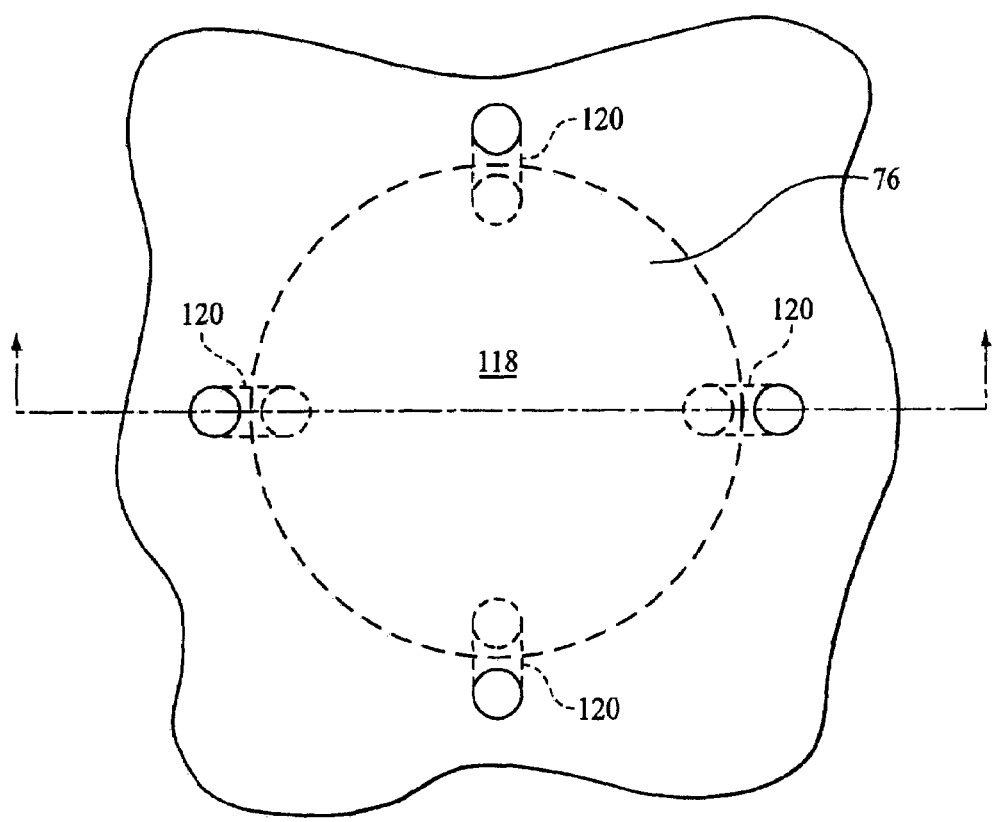
FIG. 24 illustrates a step in a method of manufacturing a sensor component, according to one embodiment of the invention.
Figure 25:
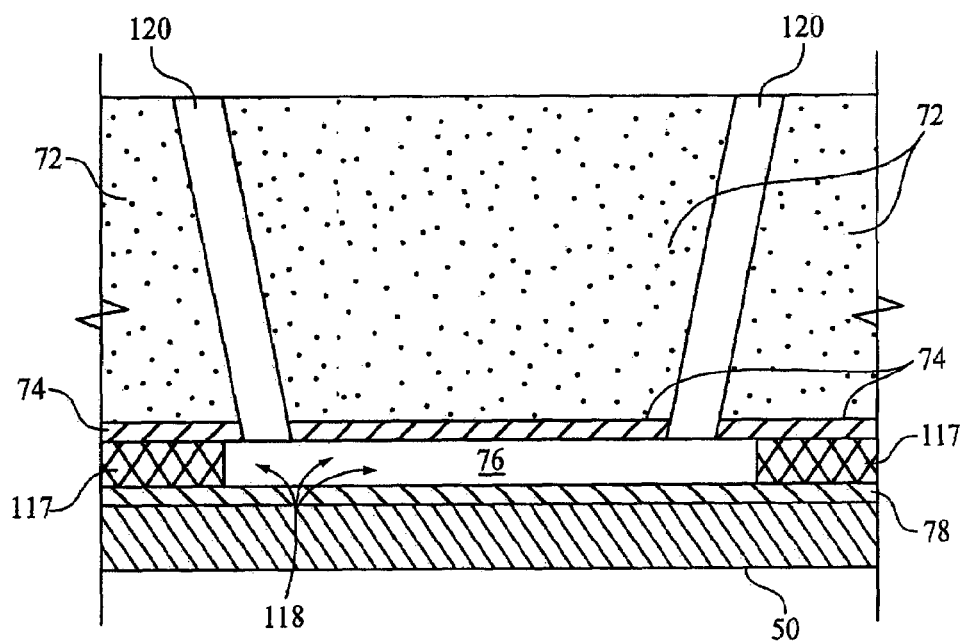
FIG. 25 illustrates a step in a method of manufacturing a sensor component, according to one embodiment of the invention.

In other instances, as is illustrate in FIGS. 24 and 25, pressure channel 76 does not include inlets. In these instances, after exposing layer of photoresist 114, one or more holes 120 are punched through substrate layer 72 and first reflective layer 74 to enable unexposed photoresist from layer of photoresist 114 to be cleaned out from the space between first and second reflective layers 74 and 78. The removal of the undeveloped photoresist from between reflective layers 74 and 78 forms pressure channel 76. The developed portions of layer of photoresist 114 form the spacers that supports first and second reflecting layers 74 and 78. In one embodiment, holes 120 are made using a laser. For example, a $CO_2$ laser may be used.

Figure 26:
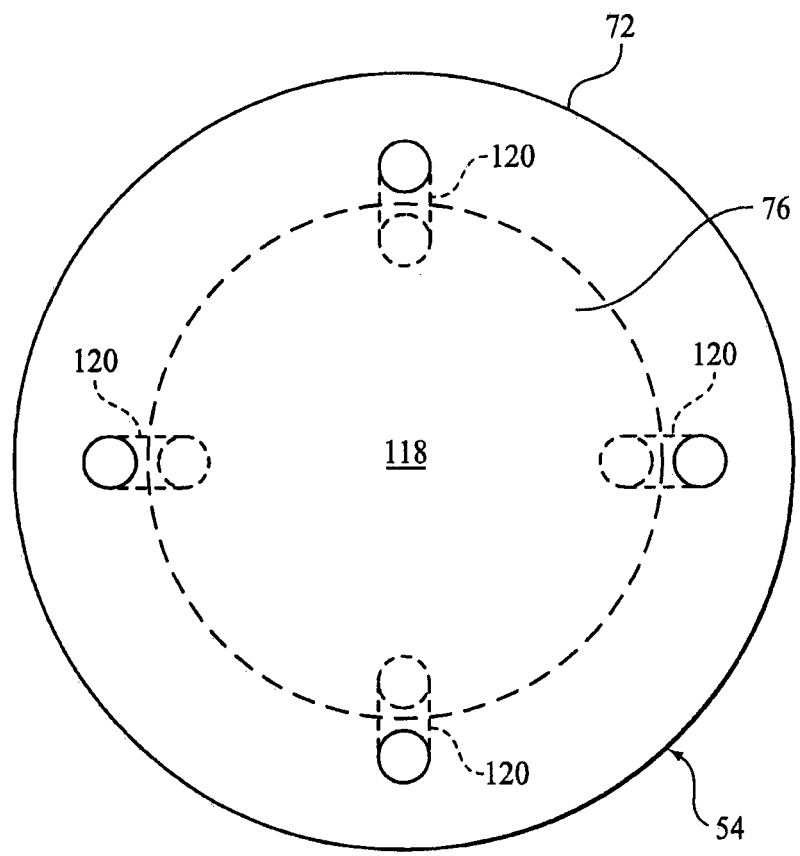
FIG. 26 illustrates a step in a method of manufacturing a sensor component, according to one embodiment of the invention.

To form individual sensor components such as sensor component 70 illustrated in FIG. 26, the portions of the substrate formed from layers 74, 114, 78, and 50 that include pressure channels are individually removed from the substrate. To remove individual sensor components from the substrate, the individual components are cut out in a convenient shape (e.g., a circle).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sensor assembly comprising:
   (a) a housing comprising:
      (i) a flow path,
      (ii) a first pressure port that communicates with the flow path, and
      (iii) a second pressure port that communicates with the flow path, wherein the first pressure port is spaced apart from the second pressure port;
      (iv) a channel that runs from the first pressure port to the second pressure port,
   (b) a flow restriction disposed in the flow path between the first and second pressure ports and that creates a pressure differential therebetween; and
   (c) a pressure transducer comprising a diaphragm disposed in the channel to substantially seal the first pressure port from the second pressure port such that the pressure differential between the first pressure port and the second pressure port causes a deformation of the diaphragm, wherein the pressure transducer generates a signal that reflects the differential pressure created by the flow restriction between the first and second pressure ports, and wherein the pressure transducer also comprises an optical interferometer.

2. The sensor assembly of claim 1, further comprising: a detection chamber disposed within the flow path, the detection chamber having a pair of transmissive windows comprising a material at least partially transmissive for a selected wavelength, such that, during operation, a beam of radiation of the selected wavelength passes through the windows and traverses the detection chamber to be detected by a photodetector, the detected radiation being useable for measuring a constituent of a gas flowing through the detection chamber.

3. The sensor assembly of claim 2, wherein the flow restriction includes differences in cross sectional area between the detection chamber and one or more other portions of the flow path.

4. The sensor assembly of claim 1, wherein at least a portion of the pressure transducer is disposed within the channel.

5. The sensor assembly of claim 4, wherein the signal generated by the pressure transducer that reflects the pressure differential created by the flow restriction between the first and second pressure ports comprises a signal generated by the optical interferometer that reflects the deformation of the diaphragm.

6. The sensor assembly of claim 5, further comprising a transmissive window formed in a wall of the channel, wherein the optical interferometer comprises:
  (i) a source that emits electromagnetic radiation through the transmissive window formed in the wall of the channel toward the diaphragm, and
  (ii) a photodetector photodeeter that receives electromagnetic radiation from the diaphragm through the transmissive window formed in the wall of the channel, and wherein the signal generated by the optical interferometer that reflects the deformation of the diaphragm comprises a signal generated by the photodetector that reflects one or more characteristics of the electromagnetic radiation received by the photodetector.

7. The sensor assembly of claim 6, wherein one or more characteristics of the electromagnetic radiation comprise an intensity of the electromagnetic radiation and/or a phase of the electromagnetic radiation.

8. The sensor assembly of claim 1, wherein the flow path is structured to conduct a respiratory gas flow and wherein the first pressure port comprises a member structured to reduce ingress of moisture from the flow path into the channel.

9. The sensor assembly of claim 5, wherein the diaphragm is disposed at the first pressure port or the second pressure port.

* * * * *